(12) United States Patent
Baba et al.

(10) Patent No.: US 8,765,719 B2
(45) Date of Patent: Jul. 1, 2014

(54) THERAPEUTIC DRUG FOR ADULT T-CELL LEUKEMIA

(75) Inventors: Masanori Baba, Kagoshima (JP); Yuichi Hashimoto, Tokyo (JP)

(73) Assignee: Kagoshima University, Kagoshima (JP)

( * ) Notice: Subject to any disclaimer, the term of this patent is extended or adjusted under 35 U.S.C. 154(b) by 223 days.

(21) Appl. No.: 13/120,114

(22) PCT Filed: Aug. 20, 2009

(86) PCT No.: PCT/JP2009/064557
§ 371 (c)(1),
(2), (4) Date: Mar. 21, 2011

(87) PCT Pub. No.: WO2010/032582
PCT Pub. Date: Mar. 25, 2010

(65) Prior Publication Data
US 2011/0172185 A1 Jul. 14, 2011

(30) Foreign Application Priority Data

Sep. 22, 2008 (JP) ................. 2008-242867
Oct. 1, 2008 (JP) ................. 2008-256620
Mar. 19, 2009 (JP) ................. 2009-068750

(51) Int. Cl.
*A61K 31/12* (2006.01)
*A61K 31/166* (2006.01)
*A61K 31/11* (2006.01)
*A61K 31/695* (2006.01)
*A61K 31/352* (2006.01)
*A61K 31/095* (2006.01)
*A61K 31/135* (2006.01)
*C07C 49/83* (2006.01)
*C07C 325/02* (2006.01)
*C07C 233/65* (2006.01)
*C07C 47/546* (2006.01)
*C07F 7/08* (2006.01)
*C07C 225/18* (2006.01)

(52) U.S. Cl.
USPC ............ 514/63; 514/682; 514/617; 514/700; 514/455; 514/706; 514/649; 568/328; 568/20; 568/440; 564/180; 564/344; 556/432; 549/389

(58) Field of Classification Search
None
See application file for complete search history.

(56) References Cited

U.S. PATENT DOCUMENTS

| | | | |
|---|---|---|---|
| 6,096,787 A | 8/2000 | Evans et al. | |
| 2003/0105333 A1* | 6/2003 | Pfahl et al. | 548/131 |
| 2008/0015252 A1 | 1/2008 | Mori | |

FOREIGN PATENT DOCUMENTS

| | | | |
|---|---|---|---|
| JP | 7-505607 | | 6/1995 |
| WO | WO 93/03713 | | 3/1993 |
| WO | WO 03/062369 | * | 7/2003 |
| WO | WO-03062369 | * | 7/2003 |
| WO | WO2004/048391 | | 6/2004 |

OTHER PUBLICATIONS

Springer et al. "Biaryl Diacid Inhibitors of Human s-PLA2 with Anti-inflammatory Activity", Bioorganic & Medicinal Chemistry 8 (2000) 1087-1109 (p. 1090, compound 16).*

Ettmayer et al. "Lessons learned from Market and investigational Prodrugs," Journal of Medicinal of Chemistry, 2004, vol. 47, 2393-2404 (p. 2394).*

Ebisawa et al. "Retinoid X Receptor-Antagonistic Diazepinylbenzoic Acids", Chem. Parm. Bull. 1999, 47 (12) 1778-1786 (p. 1778).*

Okudaira et al. "NIK-333 inhibts growth of human T-cell leukemia virus type I-infected T-cell line and adult T-cell leukemia cells in association with blockade of nuclear factor-kB signal pathway", Molecular Cancer Therapeutics, 2006, 704-712 (p. 707-708 and 710).*

Okudaira et al. "NIK-333 inhibts growth of human T-cell leukemia virus type I-infected T-cell line and adult T-cell leukemia cells in association with blockade of nuclear factor-kB signal pathway", Molecular Cancer Therapeutics, 2006, 704-712.*

Ebisawa et al. "Retinoid X Receptor-Antagonistic Diazepinylbenzoic Acids", Chem. Parm. Bull. 1999, 47 (12) 1778-1786.*

Matutes, "Adult T-cell leukaemia / lymphoma", J. Clin. Pathol., 2007, 60, 1373-1377.*

Kagechika, Hiroyuki, et al., "Retinobenzoic Acids. 2. Structure-Activity Relationships of Chalcone-4-carboxylic Acids and Flavone-4'-carboxylic Acids", Journal of Medicinal Chemistry, vol. 32, No. 4, 1989, pp. 834-840.

Nakamura, Masahiko, et al., "Discovery of tetrahydrotetramethylnaphthalene analogs as adult T-cell leukemia cell-selective proliferation inhibitors in a small chemical library constructed based on multi-template hypothesis", Bioorganic & Medicinal Chemistry, 17, (2009), pp. 4740-4746.

IUPAC-IUB Joint Commission on Biochemical Nomenclature (JCBN), Eur. J. Biochem., 129: 1-5 (1982).

M. B. Sporn, "Mechanism of actoin of retinoids," J. Amer. Acad. Dermatol., 15: 756-764 (1986).

M. Petkovich, "A human retinoic acid receptor which belongs to the family of nuclear receptors," Nature, 330: 444-450 (1987).

H Kagechika, "Retinobenzoic acid. 2. Structure-Activity relationships of chalcone-4-carboxylic acids and flavone-4'-carboxylic acids," J. Med. Chem. 1989, 32, 834-840.

\* cited by examiner

*Primary Examiner* — Ernst Arnold
*Assistant Examiner* — Jianfeng Song
(74) *Attorney, Agent, or Firm* — McCarter & English

(57) ABSTRACT

An object is to provide a novel therapeutic drug for adult T-cell leukemia having an ATL cell specific antitumor effect. The therapeutic drug for adult T-cell leukemia according to the invention is characterized by containing a compound represented by the formula I or a prodrug thereof,

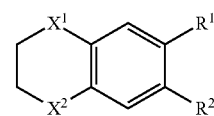

I wherein $R^1$ is H, OH, an alkoxy group, an acyl group, or a thioacyl group, $R^2$ is an acyl group, a thioacyl group, $CONR^7R^8$, or $CSNR^7R^8$ ($R^7$ and $R^8$ being each independently H, an alkyl group containing 1 to 3 carbon atoms, or a phenyl group), or $R^1$ and $R^2$ together may form a ring, $X^1$ and $X^2$ may be the same or different and are each —$CR^3R^4$—, —$SiR^3R^4$— or oxygen, and $R^3$ and $R^4$ may be the same or different and are each an alkyl group containing 1 to 6 carbon atoms.

10 Claims, 1 Drawing Sheet

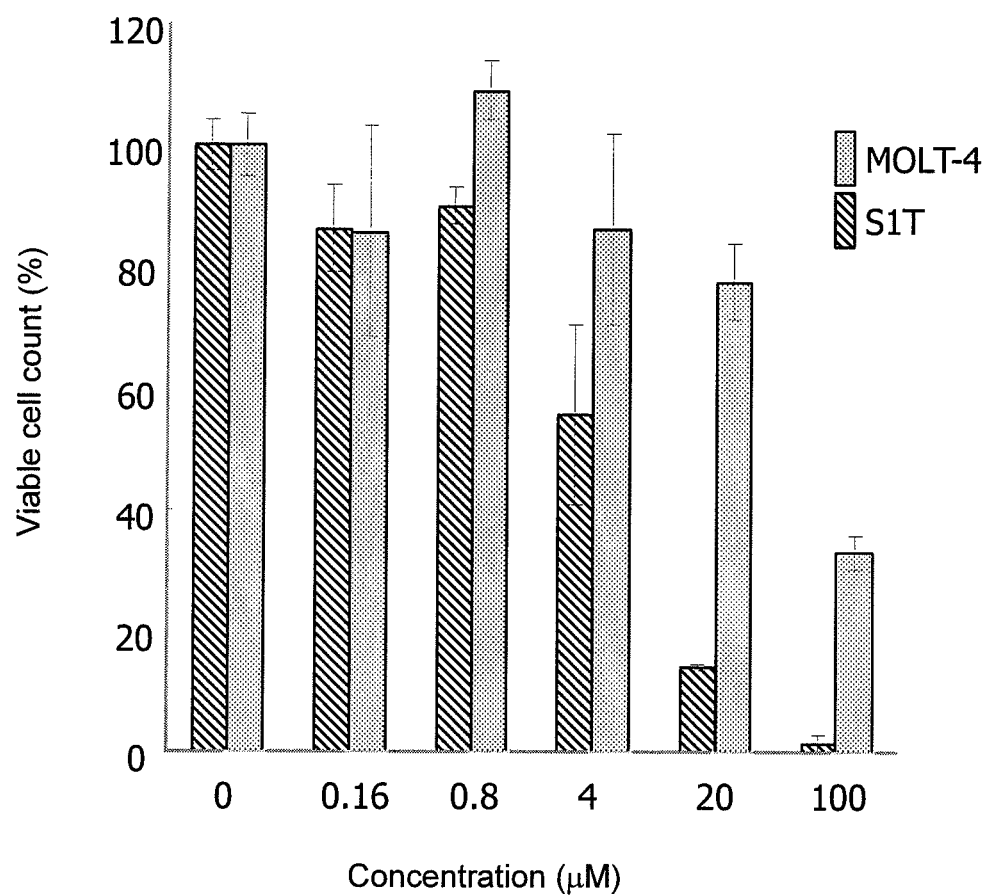

THERAPEUTIC DRUG FOR ADULT T-CELL LEUKEMIA

RELATED APPLICATIONS

This application is a national stage application filed under 35 USC 371 of PCT/JP2009/064557, filed Aug. 20, 2009, which claims the benefit of Japanese Patent Application No. 2008-242867, filed Sep. 22, 2008, Japanese Patent Application No. 2008-256620, filed Oct. 1, 2008, and Japanese Patent Application No. 2009-068750, filed Mar. 19, 2009, all of which are incorporated herein, in entirety, by reference.

TECHNICAL FIELD

The present invention relates to an agent used for treating adult T-cell leukemia (ATL).

BACKGROUND ART

Adult T-cell leukemia (ATL) is a malignant tumor caused by infection with HTLV-1. It is estimated that the number of carriers of HTLV-1 is about 1.2 millions in Japan and 10 to 20 millions in the world, and believed that 2 to 5% of them develop ATL in their lives. The survival rate after the onset of ATL is extremely low, and although a multidrug therapy using various anticancer drugs has been conducted as a treatment, the treatment outcome is poor due to rapid acquisition of drug resistance.

As a conventional therapeutic drug for adult T-cell leukemia, for example, Patent Literature 1 discloses a therapeutic agent containing fucoxanthin or fucoxanthinol as an active ingredient. Further, Patent Literature 2 discloses a therapeutic agent for adult T-cell leukemia containing digitoxin as an active ingredient.

Under such circumstances, development of a new agent having specificity to an ATL cell has been demanded.

CITATION LIST

Patent Literature

Patent Literature 1: Japanese Patent Publication (Kokai) No. 2008-19174 A
Patent Literature 2: Japanese Patent Publication (Kokai) No. 4-36240 A (1992)

SUMMARY OF INVENTION

Technical Problem

Consequently, an object of the present invention is to provide a novel therapeutic drug for adult T-cell leukemia having an ATL cell specific antitumor effect.

Solution to Problem

To achieve the object, the present inventors have screened an agent library using a cell strain S1T established from an ATL patient to try to identify an agent having an ATL cell specific antitumor effect, and found selective ATL cell growth suppression activity in agents having a certain structure, thereby completing the present invention. More specifically, the summary of the present invention is as follows.

(1) A therapeutic drug for adult T-cell leukemia comprising a compound represented by the formula I or a prodrug thereof:

[Formula 1]

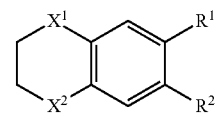

I wherein $R^1$ is H, OH, an alkoxy group, an acyl group, or a thioacyl group, $R^2$ is an acyl group, a thioacyl group, $CONR^7R^8$, or $CSNR^7R^8$ ($R^7$ and $R^8$ being each independently H, an alkyl group containing 1 to 3 carbon atoms, or a phenyl group), or $R^1$ and $R^2$ together may form a ring, $X^1$ and $X^2$ may be the same or different and are each $—CR^3R^4—$, $—SiR^3R^4—$ or oxygen, and $R^3$ and $R^4$ may be the same or different and are each an alkyl group containing 1 to 6 carbon atoms.

(2) The therapeutic drug for adult T-cell leukemia according to (1) above, wherein the compound represented by the formula I is a compound represented by the formula II:

[Formula 2]

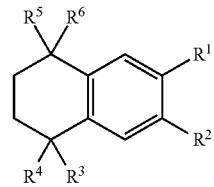

II wherein $R^1$ is H, or OH, $R^2$ is an acyl group, and $R^3$ to $R^6$ may be the same or different and are each an alkyl group containing 1 to 6 carbon atoms.

(3) The therapeutic drug for adult T-cell leukemia according to (2) above, wherein the compound represented by the formula II is a compound represented by the formula III:

[Formula 3]

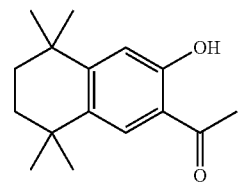 [SMILES: CC(=O)c1cc2c(cc1O)C(C)(C)CCC2(C)C]

III (4) The therapeutic drug for adult T-cell leukemia according to (2) above, wherein the compound represented by the formula II is a compound represented by the formula IV:

[Formula 4]

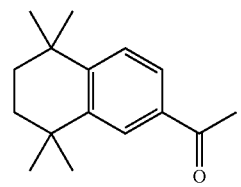

IV (5) The therapeutic drug for adult T-cell leukemia according to (1) above, wherein the compound represented by the formula I is a compound represented by the formula V or the formula VI:

[Formula 5]

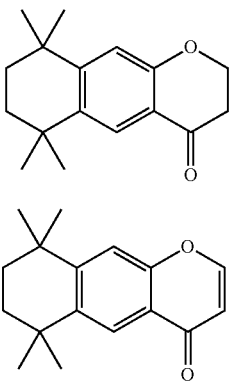

Advantageous Effects of Invention

Since the compound according to the present invention can suppress selectively the growth of an ATL cell strain, the same is consequently effective as a therapeutic drug for adult T-cell leukemia.

BRIEF DESCRIPTION OF DRAWINGS

FIG. 1 is a graph showing the selective ATL cell growth suppression activity of the compound (TMNAA) according to the formula III.

DESCRIPTION OF EMBODIMENTS

The present invention will be described in detail below.

A therapeutic drug for adult T-cell leukemia according to the present invention is characterized by containing a compound represented by the formula I as an active ingredient, wherein $R^1$ is H, OH, an alkoxy group, an acyl group, or a thioacyl group, $R^2$ is an acyl group, a thioacyl group, $CONR^7R^8$, or $CSNR^7R^8$ ($R^7$ and $R^8$ being each independently H, an alkyl group containing 1 to 3 carbon atoms, or a phenyl group), or $R^1$ and $R^2$ together may form a ring, $X^1$ and $X^2$ may be the same or different and are each —$CR^3R^4$—, —$SiR^3R^4$— or oxygen, and $R^3$ and $R^4$ may be the same or different and are each an alkyl group containing 1 to 6 carbon atoms. A compound, in which $X^1$ and $X^2$ are oxygen (O), is commercially available from Sigma-Aldrich, Inc.:

[Formula 6]

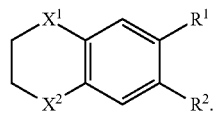

The alkoxy group may be either linear or branched, and preferably contains 1 to 5 carbon atoms. Examples of such alkoxy group may include a methoxy group, an ethoxy group, a propyloxy group, an i-propyloxy group, a butoxy group, an i-butoxy group, a t-butoxy group, and a pentyloxy group.

Examples of the acyl group include a linear or branched, saturated or unsaturated aliphatic acyl group containing 1 to 10 carbon atoms, such as a formyl group, an acetyl group, a propionyl group, a butyryl group, an isobutyryl group, a valeryl group, an isovaleryl group, a pivaloyl group, a hexanoyl group, an octanoyl group, a decanoyl group, a propenoyl group (acryloyl group), a butenoyl group, an isobutenoyl group, a pentenoyl group, a hexenoyl group, and a 4-methyl-2-pentenoyl group; and preferably a saturated or unsaturated aliphatic acyl group containing 2 to 10 carbon atoms (the carbon number is a number including the carbon in a carbonyl group); and an aromatic acyl group (an aroyl group), such as a benzoyl group, and a naphthoyl group.

Examples of the applicable thioacyl group include those derived from the aforedescribed acyl groups by replacing the carbonyl group with a thiocarbonyl group, and more specifically a thioformyl group, a thioacetyl group, a thiopropionyl group, a thiobutyryl group, and a thiobenzoyl group.

In the aforedescribed acyl groups or thioacyl groups, a carbon atom not adjacent to a carbonyl group or a thiocarbonyl group may be replaced with a hetero atom, such as nitrogen, sulfur, and oxygen. Examples of such an acyl group or a thioacyl group replaced with a hetero atom include —COCH=CHN(CH$_3$)$_2$, and —CSCH=CHN(CH$_3$)$_2$.

Examples of the $CONR^7R^8$ group and $CSNR^7R^8$ include $CONH_2$, $CONH(CH_3)$, $CON(CH_3)_2$, $CONH(CH_2CH_3)$, $CONH(CH_2CH_2CH_3)$, $CONHC(CH_3)_3$, $CONHC_6H_5$, $CSNH_2$, $CSNH(CH_3)$, $CSN(CH_3)_2$, $CSNH(CH_2CH_3)$, $CSNH(CH_2CH_2CH_3)$, $CSNHC(CH_3)_3$, and $CSNHC_6H_5$. Among them is especially preferable $CONH_2$.

The alkyl group containing 1 to 6 carbon atoms may be linear or branched, and examples thereof include a methyl group, an ethyl group, an n-propyl group, an isopropyl group, an n-butyl group, a t-butyl group, an isobutyl group, an n-pentyl group, an isopentyl group, and a neopentyl group.

A preferable embodiment of the therapeutic drug for adult T-cell leukemia according to the present invention is characterized by containing a compound represented by the formula II as an active ingredient, wherein $R^1$ is H or OH, $R^2$ is an acyl group, and $R^3$ to $R^6$ may be the same or different and are each an alkyl group containing 1 to 6 carbon atoms:

[Formula 7]

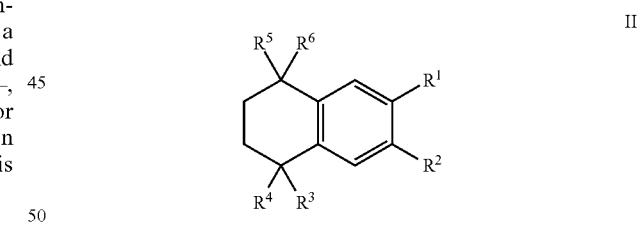

The acyl group is as defined above, and examples thereof include a linear or branched, saturated or unsaturated aliphatic acyl group containing 1 to 10 carbon atoms, such as a formyl group, an acetyl group, a propionyl group, a butyryl group, an isobutyryl group, a valeryl group, an isovaleryl group, a pivaloyl group, a hexanoyl group, an octanoyl group, a decanoyl group, a propenoyl group, a butenoyl group, an isobutenoyl group, a pentenoyl group, a hexenoyl group, and a 4-methyl-2-pentenoyl group; and preferably a saturated or unsaturated aliphatic acyl group containing 2 to 10 carbon atoms (the carbon number is a number including the carbon in a carbonyl group); and an aromatic acyl group (an aroyl group), such as a benzoyl group, and a naphthoyl group.

The alkyl group containing 1 to 6 carbon atoms may be, as described above, either linear or branched, and examples thereof include a methyl group, an ethyl group, an n-propyl group, an isopropyl group, an n-butyl group, a t-butyl group, an isobutyl group, an n-pentyl group, an isopentyl group, and a neopentyl group.

Especially, the therapeutic drug for adult T-cell leukemia according to the present invention preferably contains as an active ingredient the compound represented by the formula III among the compounds according to the above formula II:

[Formula 8]

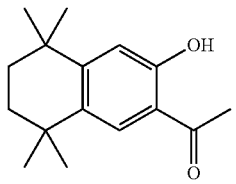

III

The compound can be synthesized by a conventional organic synthesis, for example according to the description of Kagechika H, Hashimoto Y, Kawachi E, Shudo K, "Affinity gels for purification of retinoid-specific binding protein (RSBP)", Biochem. Biophys. Res. Commun. 155: 503-508 (1988). Specifically, the objective compound of the formula III (5,6,7,8-tetrahydro-3-hydroxy-5,5,8,8-tetramethyl-2-naphthyl methyl ketone) can be yielded according to the following reaction formula by heating 5,6,7,8-tetrahydro-5,5,8,8-tetramethyl-2-naphthyl methyl ketone with m-chloroperbenzoic acid (mCPBA) in chloroform for several hours, and by heating the yielded intermediate with aluminum chloride at 130 to 140° C.:

[Formula 9]

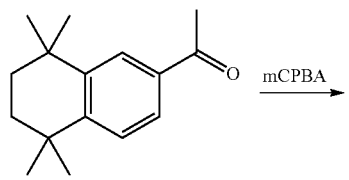

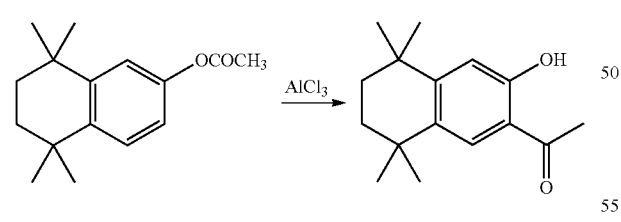

The acetyl group in the compound of the formula III can be converted to a thioacetyl group according to the method described in Hupp C D, Tepe J J, "Total Synthesis of a Marine Alkaloid from the Tunicate *Dendrodoa grossularia*", Org. Lett. 10: 3737-3739 (2008). Specifically, 5,6,7,8-tetrahydro-3-hydroxy-5,5,8,8-tetramethyl-2-naphthyl ethanethione can be yielded according to the following reaction formula by heating under reflux 5,6,7,8-tetrahydro-3-hydroxy-5,5,8,8-tetramethyl-2-naphthyl methyl ketone with Lawesson's reagent in toluene:

[Formula 10]

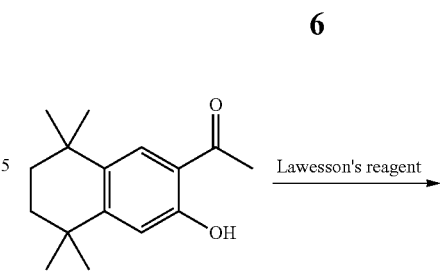

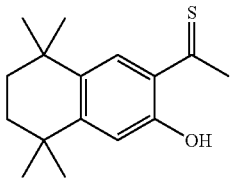

In another embodiment, the therapeutic drug for adult T-cell leukemia according to the present invention contains preferably a compound represented by the formula IV as an active ingredient:

[Formula 11]

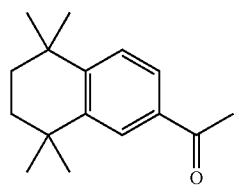 [SMILES: CC(=O)c1ccc2c(c1)C(C)(C)CCC2(C)C]

IV

The compound can be synthesized by a conventional organic synthesis, for example according to the description of Kagechika H, Kawachi E, Hashimoto Y, Himi T, Shudo K, "Retinobenzoic acids. 1. Structure-activity relationships of aromatic amides with retinoidal activity", J. Med. Chem. 31: 2182-2192 (1988), or Buttner M W, Penka M, Doszczak L, Kraft P, Tacke R, "Silicon analogues of the musk odorant veralide", Organometallics, 26: 1295-1298 (2007). Specifically, the objective compound of the formula IV (5,6,7,8-tetrahydro-5,5,8,8-tetramethyl-2-naphthyl methyl ketone) can be obtained at a yield of about 80% according to the following reaction formula by reacting 1,2,3,4-tetrahydro-1,1,4,4-tetramethylnaphthalene with acetyl chloride in dichloroethane in the presence of aluminum chloride:

[Formula 12]

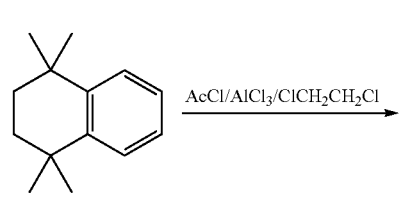

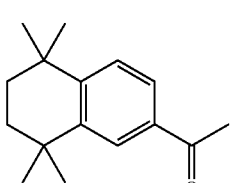

Further, in another embodiment, the therapeutic drug for adult T-cell leukemia according to the present invention contains preferably a compound represented by the formula V or the formula VI as an active ingredient:

[Formula 13]

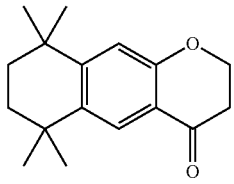

V

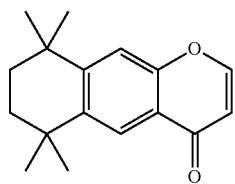

VI

The compound of the formula V is equivalent to that with OH as the $R^1$ and a propionyl group as the $R^2$, which form together a ring, and the compound of the formula VI is equivalent to that with OH as the $R^1$ and a propenoyl group as the $R^2$, which form together a ring.

As another example of the therapeutic drug for adult T-cell leukemia according to the present invention, the compound represented by the formula VII may be quoted:

[Formula 14]

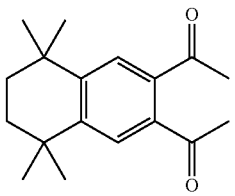

VII

A prodrug of a compound represented by the formulas I to VII means a compound to be converted to the compound of the formulas I to VII under physiological conditions in vivo according to a reaction by an enzyme, gastric acid, or the like, more particularly a compound to be converted to the compound of the formulas I to VII enzymatically by oxidation, reduction, hydrolysis, etc., or a compound to be converted to the compound of the formulas I to VII, for example, through hydrolysis by gastric acid. For example, examples of a prodrug of the compound according to the formula III include a compound derived by acylation, alkylation, phosphorylation, or boration of the hydroxy group of the compound according to the formula III (e.g. a compound derived by acetylation, palmitoylation, propanoylation, pivaloylation, succinylation, fumarylation, alanylation or dimethylaminomethylcarbonylation of the hydroxy group of the compound according to the formula III). Such prodrug can be produced by a per se publicly known method from the compound according to the formula III.

Examples of prodrugs of the compounds according to the formulas V and VI include compounds represented by the following formulas:

[Formula 15]

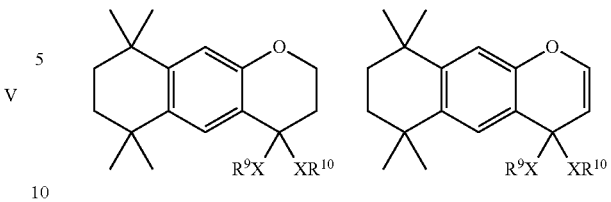

wherein X is O or S, $R^9$ and $R^{10}$ are H, $CH_3$, etc., or $R^9$ and $R^{10}$ may together form a ring.

Further, a compound represented by the following formula may be used as a prodrug of the compound according to the formula V:

[Formula 16]

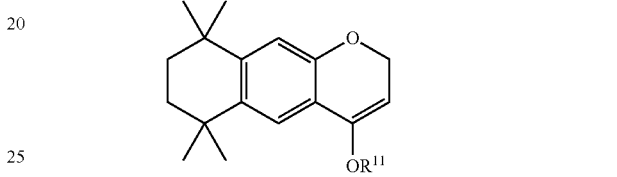

wherein $R^{11}$ is an alkyl group such as $CH_3$, or an acyl group such as $COCH_3$.

Further, a prodrug of a compound of the formulas I to VII may be converted to the compound of the formulas I to VII under physiological conditions as described in "Pharmaceutical Research and Development (Iyakuhin no Kaihatsu)", Vol. 7 (Molecular Design), HirokawaShoten, 1990, p. 163-198.

The compound or a prodrug thereof may be formulated in combination with a conventional pharmaceutical carrier to form a therapeutic drug for adult T-cell leukemia. There is no particular restriction on a dosage form, which can be selected appropriately according to need, and examples thereof include an oral preparation, such as a tablet, a capsule, a granule, a fine granule, a powder, a sustained release preparation, a liquid, a suspension, an emulsion, a syrup, and an elixir, and a parenteral preparation, such as an injection, and a suppository.

An oral preparation can be produced according to a conventional method using starch, lactose, white soft sugar, mannitol, carboxymethylcellulose, corn starch, inorganic salts, etc.

In addition to the aforementioned excipients, a binder, a disintegrator, a surfactant, a lubricant, a glidant, a corrigent, a colorant, a fragrance, etc. may be admixed appropriately.

Examples of a binder include starch, dextrin, gum arabic, gelatin, hydroxypropyl starch, methylcellulose, sodium carboxymethylcellulose, hydroxypropylcellulose, crystalline cellulose, ethylcellulose, polyvinylpyrrolidone, and macrogol.

Examples of a disintegrator include starch, hydroxypropyl starch, sodium carboxymethylcellulose, calcium carboxymethylcellulose, carboxymethylcellulose, and low substituted hydroxypropylcellulose.

Examples of a surfactant include sodium lauryl sulfate, soybean lecithin, sucrose fatty acid ester, and polysorbate 80.

Examples of a lubricant include talc, waxes, a hydrogenated plant oil, sucrose fatty acid ester, magnesium stearate, calcium stearate, aluminum stearate, and polyethylene glycol.

Examples of a glidant include light anhydrous silicic acid, dried aluminum hydroxide gel, synthetic aluminum silicate, and magnesium silicate.

An injection can be produced according to a conventional method, and as a diluent therefor can be used in general distilled water for injection, physiologic saline, a glucose aq. solution, an olive oil, a sesame oil, an earth nut oil, a soybean oil, a corn oil, propylene glycol, polyethylene glycol, etc. Further, according to need, a bactericide, a preservative, a stabilizer, an isotonizing agent, a soothing agent, etc. may be added. Furthermore, from a standpoint of stability, an injection may be filled in a vial, etc., frozen and subjected to usual freeze-drying to remove water. A liquid can be reprepared from the freeze-dried product immediately before use. The content of a compound according to the formulas I to VII or a prodrug thereof in an injection may vary, without limited thereto, in a range of 5 to 50 weight-%.

Examples of another parenteral preparation include a suppository for intrarectal administration, which can be produced according to a conventional method.

A formulated therapeutic drug may be administered 1 to 4 times per day and for 1 week to 3 months, subject to a formulation form, an administration route, etc.

An oral preparation should preferably be taken to exert a desired effect for an adult generally in an amount of 0.1 to 1000 mg, preferably 1 to 500 mg, as the mass of a compound or a prodrug thereof according to the formula I to VII, which may be divided into several doses per day, thought the amount may be varied in accordance with the age, body mass, or severity of disease of the patient.

A parenteral preparation should preferably be administered by intravenous injection, intravenous drip infusion, subcutaneous injection, or intramuscular injection to exert a desired effect for an adult generally in an amount of 0.1 to 1000 mg, preferably 1 to 500 mg, as the mass of a compound or a prodrug thereof according to the formulas I to VII, though the amount may be varied in accordance with the age, body mass, or severity of disease of the patient.

EXAMPLES

The present invention will be described below in more detail based on Examples and Comparative Examples, provided that the same should not be interpreted in any restrictive way.

Examples and Comparative Examples

In the presence of various agents, S1T (cell strain originated from an ATL patient), MT-2 (HTLV-1 infected cell strain), and as controls, MOLT-4 (acute lymphoblastic leukemia cell strain), CEM (acute lymphoblastic leukemia cell strain), HL-60 (acute promyelocytic leukemia cell strain), and Jurkat (acute T-cell leukemia cell strain) were cultivated for 4 days, and the growth inhibitory effects of compounds on the respective cells were evaluated by the MIT method.

With S1T and MOLT-4 were screened 138 agents to find that the inhibitory concentrations 50% ($IC_{50}$) on S1T were 0 to 1 µM for 7 agents, 1 to 10 µM for 26 agents, and 10 to 100 µM for 67 agents. Meanwhile, the same on MOLT-4 were 0 to 1 µM for 8 agents, 1 to 10 µM for 32 agents, and 10 to 100 µM for 67 agents. Among them, as an agent inhibiting specifically the growth of an ATL cell strain, 6 agents with the selectivity index on the S1T cell (SI=$IC_{50}$ for MOLT-4/$IC_{50}$ for S1T) of 2 or higher, and 1 agent with the same of 10 or higher were identified. The results of the compound (TMNAA) according to the formula III, which gave the SI of 10 or higher, are shown in FIG. 1. Incidentally, TMNAA was synthesized according to the description of Kagechika H, Hashimoto Y, Kawachi E, Shudo K, "Affinity gels for purification of retinoid-specific binding protein (RSBP)", Biochem. Biophys. Res. Commun. 155: 503-508 (1988). As obvious from FIG. 1, TMNAA, a compound according to the present invention, inhibits selectively at a concentration of 4 µM or higher the growth of an ATL cell in comparison to the control.

Further, the results of the compound ($TMN(COCH_3)$) according to the formula IV, which gave a high SI value similarly as TMNAA, and other derivatives are shown in Table 1. As obvious from Table 1, the compounds according to the present invention, TMNAA, $TMN(COCH_3)$ and $TMN(OCH_3)(COCH_3)$, have higher selectivity to an ATL cell than other derivatives with analogous structures. Among them, TMNAA and $TMN(COCH_3)$, which are the compounds according to the present invention, have been found to have higher selectivity to an ATL cell than other derivatives with analogous structures. Meanwhile, despite a report on anti-ATL effect of sodium salicylate, which is an agent related to the above compounds, by Portis T, Harding J C, Ratner L, "The contribution of NF-κB activity to spontaneous proliferation and resistance to apoptosis in human T-cell leukemia virus type 1 Tax-induced tumors", Blood 98: 1200-1208 (2001), no selectivity to S1T was recognized by the experiment as shown in Table 1. With the compound of the formula III, which gave the SI above 10, the growth inhibitory effects on MT-2, CEM, HL-60, and Jurkat were studied to find that it gave a specific inhibitory effect solely on MT-2.

TABLE 1

| Agent | | $IC_{50}$ (µM) | | |
|---|---|---|---|---|
| Designation | Chemical structure | S1T | MOLT-4 | SI |
| Sodium salicylate | | 1,570 | 1,320 | 0.84 |
| TNBAA | | 29.7 | 44.4 | 1.49 |
| TMNAA | | 5.0 | 53.8 | 10.8 |
| TMBA | | >100 | 61.1 | <0.61 |
| TMN(COCH$_3$) | | 6.9 | 66.0 | 9.6 |

TABLE 1-continued

| Agent | | IC$_{50}$ (μM) | | |
|---|---|---|---|---|
| Designation | Chemical structure | S1T | MOLT-4 | SI |
| TMN(OCH$_3$)(COCH$_3$) | 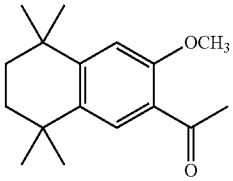 [SMILES: COc1cc2c(cc1C(C)=O)C(C)(C)CCC2(C)C] | 7.0 | 11.9 | 1.7 |
| TMN | 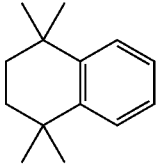 | >100 | >100 | <>1 |

IC50: Concentration of an agent to inhibit cell growth by 50%
SI: Selectivity to ALT cell Example 1

Synthesis of 5,6,7,8-tetrahydro-3-hydroxy-5,5,8,8-tetramethyl-2-naphthyl ethyl ketone (A)

(1) Synthesis of 5,6,7,8-tetrahydro-2-hydroxy-5,5,8,8-tetramethyl naphthalene (a)

The synthesis process is as set forth in the chemical reaction formula below. The AlCl$_3$ in the reaction path stands for aluminum chloride. Into phenol (1.02 g, 10.8 mmol) were added anhydrous dichloromethane (5 mL), aluminum chloride (144 mg, 1.08 mmol), and 2,5-dichloro-2,5-dimethylhexane (2.18 g, 11.9 mmol) followed by stirring at room temperature for 19 hours. The reaction solution was poured into cold water and extracted by ethyl acetate. The organic layer was washed by water, a saturated sodium hydrogen carbonate aq. solution, and a saturated saline solution, dried over magnesium sulfate, and concentrated under reduced pressure. The crude product was purified by recrystallization in a solvent of hexane. The yield was 1.83 g (83%).

FAB-MS m/z 204 (M+H)$^+$; $^1$H-NMR (500 MHz, CDCl$_3$) δ 7.17 (d, 1H, J=8.5 Hz), 6.75 (d, 1H, J=3.0 Hz), 6.62 (dd, 1H, J=5.5, 3.0 Hz), 4.49 (s, 1H), 1.66 (s, 4H), 1.25 (s, 6H), 1.24 (s, 6H).

(2) Synthesis of 5,6,7,8-tetrahydro-3-hydroxy-5,5,8,8-tetramethyl-2-naphthyl ethyl ketone (A)

To 5,6,7,8-tetrahydro-2-hydroxy-5,5,8,8-tetramethylnaphthalene (204 mg, 1.00 mmol) were added anhydrous dichloromethane (1 mL), aluminum chloride (148 mg, 1.12 mmol), and propionyl chloride (101.7 mg, 1.10 mmol) followed by stirring at 60° C. for 16 hours. The reaction solution was poured into cold water and extracted by ethyl acetate. The organic layer was washed by water, a saturated sodium hydrogen carbonate aq. solution, and a saturated saline solution, dried over magnesium sulfate, and concentrated under reduced pressure. The crude product was purified by silica gel column chromatography using hexane/ethyl acetate (20/1) as an elution solvent. The yield was 117 mg (45%).

FAB-MS m/z 247 (M+H)$^+$; $^1$H-NMR (500 MHz, CDCl$_3$) δ 11.96 (s, 1H), 7.68 (s, 1H), 6.90 (s, 1H), 3.03 (q, 2H), 1.68 (s, 4H), 1.28 (s, 6H), 1.27 (s, 6H), 1.25 (t, 3H, J=7.3 Hz).

Example 2

Synthesis of 5,6,7,8-tetrahydro-3-hydroxy-5,5,8,8-tetramethyl-2-naphthyl isopropyl ketone (B)

The synthesis process is as set forth in the chemical reaction formula below. To 5,6,7,8-tetrahydro-2-hydroxy-5,5,8,8-tetramethylnaphthalene (204 mg, 1.00 mol) were added anhydrous dichloromethane (1 mL), aluminum chloride (148 mg, 1.12 mmol), and isobutyryl chloride (117 mg, 1.10 mmol) followed by stirring at 60° C. for 2 hours. The reaction solution was poured into cold water, and extracted by ethyl acetate. The organic layer was washed by water, a saturated sodium hydrogen carbonate aq. solution, and a saturated saline solution, dried over magnesium sulfate, and concentrated under reduced pressure. The crude product was purified by silica gel chromatography using hexane/ethyl acetate (20/1) as an elution solvent. The yield was 128 mg (47%).

FAB-MS m/z 261 (M+H)$^+$; $^1$H-NMR (500 MHz, CDCl$_3$) δ 12.11 (s, 1H), 7.71 (s, 1H), 6.91 (s, 1H), 3.60 (septet, 1H, J=7.0 Hz), 1.68 (s, 4H), 1.29 (s, 6H), 1.27 (s, 6H), 1.24 (d, 6H, J=6.7 Hz).

Example 3

Synthesis of 5,6,7,8-tetrahydro-3-hydroxy-5,5,8,8-tetramethyl-2-naphthyl tert-butyl ketone (C)

The synthesis process is as set forth in the chemical reaction formula below. The TiCl$_4$ in the reaction path stands for titanium chloride. To 5,6,7,8-tetrahydro-2-hydroxy-5,5,8,8-tetramethylnaphthalene (409 mg, 2.00 mmol) were added titanium chloride (417 mg, 2.20 mmol) and pivaloyl chloride (361 mg, 2.99 mmol) followed by stirring at 120° C. for 1 hour. The reaction solution was diluted by dichloromethane, and the organic layer was washed by water, a saturated sodium hydrogen carbonate aq. solution, and a saturated saline solution, dried over magnesium sulfate, and concentrated under reduced pressure. The crude product was purified by silica gel chromatography using hexane/ethyl acetate (40/3) as an elution solvent. The yield was 53.6 mg (9.0%).

FAB-MS m/z 289 (M+H)$^+$; $^1$H-NMR (500 MHz, CDCl$_3$) δ 12.30 (s, 1H), 7.97 (s, 1H), 6.92 (s, 1H), 2.05 (s, 1H), 1.68 (s, 4H), 1.45 (s, 9H), 1.29 (s, 6H), 1.27 (s, 6H).

Example 4

Synthesis of 5,6,7,8-tetrahydro-3-hydroxy-5,5,8,8-tetramethyl-2-naphthyl phenyl ketone (D)

The synthesis process is as set forth in the chemical reaction formula below. To 5,6,7,8-tetrahydro-2-hydroxy-5,5,8,8-tetramethylnaphthalene (204 mg, 1.00 mmol) were added anhydrous dichloromethane (1 mL), aluminum chloride (148 mg, 1.12 mmol), and benzoyl chloride (155 mg, 1.10 mmol) followed by stirring at 60° C. for 1 hour. The reaction solution was poured into cold water and extracted by ethyl acetate. The organic layer was washed by water, a saturated sodium hydrogen carbonate aq. solution, and a saturated saline solution, dried over magnesium sulfate, and concentrated under reduced pressure. The crude product was purified by silica gel chromatography using hexane/ethyl acetate (20/1) as an elution solvent. The yield was 27.3 mg (9%).

FAB-MS m/z 309 (M+H)$^+$; $^1$H-NMR (500 MHz, CDCl$_3$) δ 11.63 (s, 1H), 7.69 (s, 1H), 7.67 (s, 1H), 7.59 (m, 2H), 7.55 (m, 3H), 6.99 (s, 1H), 2.05 (s, 1H), 1.68 (m, 4H), 1.30 (s, 6H), 1.17 (s, 6H).

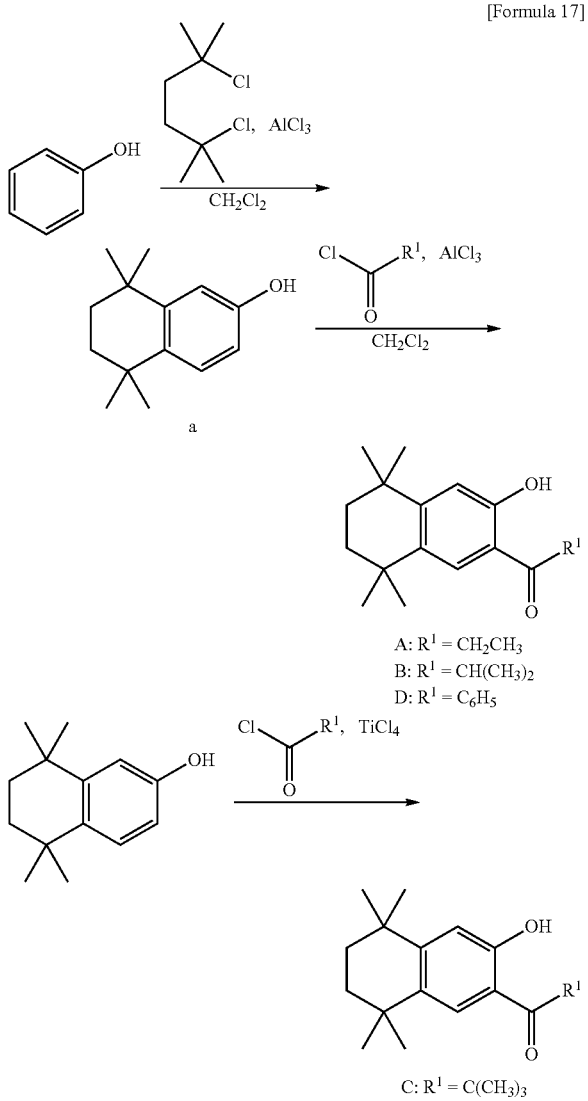

[Formula 17]

Example 5

Synthesis of 5,6,7,8-tetrahydro-5,5,8,8-tetramethyl-2-naphthyl ethyl ketone (E)

The synthesis process is as set forth in the chemical reaction formula below. To 5,6,7,8-tetrahydro-5,5,8,8-tetramethylnaphthalene (188 mg, 1 mmol) were added anhydrous dichloromethane (1 mL), aluminum chloride (148 mg, 1.12 mmol), and propionyl chloride (101 mg, 1.10 mmol) followed by stirring at 60° C. for 3 hours. The reaction solution was poured into cold water and extracted by ethyl acetate. The organic layer was washed by water, a saturated sodium hydrogen carbonate aq. solution, and a saturated saline solution, dried over magnesium sulfate, and concentrated under reduced pressure. The crude product was purified by silica gel chromatography using hexane/ethyl acetate (30/1) as an elution solvent. The yield was 66.4 mg (27%).

FAB-MS m/z 245 (M+H)$^+$; $^1$H-NMR (500 MHz, CDCl$_3$) δ 7.94 (d, 1H, J=2.0 Hz), 7.70 (dd, 1H, J=6.0, 2.0 Hz), 7.38 (d, 1H, J=8.5 Hz), 2.97 (q, 2H, J=7.3 Hz), 1.70 (s, 4H), 1.31 (s, 6H), 1.29 (s, 6H), 1.22 (t, 3H, J=7.3 Hz).

Example 6

Synthesis of 5,6,7,8-tetrahydro-5,5,8,8-tetramethyl-2-naphthyl isopropyl ketone (F)

The synthesis process is as set forth in the chemical reaction formula below. To 5,6,7,8-tetrahydro-5,5,8,8-tetramethylnaphthalene (188 mg, 1.00 mmol) were added anhydrous dichloromethane (1 mL), aluminum chloride (140 mg, 1.05 mmol), and isobutyryl chloride (112 mg, 1.05 mmol) followed by stirring at room temperature for 3 hours. The reaction solution was poured into cold water and extracted by ethyl acetate. The organic layer was washed by water, a saturated sodium hydrogen carbonate aq. solution, and a saturated saline solution, dried over magnesium sulfate, and concentrated under reduced pressure. The crude product was purified by silica gel chromatography using hexane/ethyl acetate (20/1) as an elution solvent. The yield was 97.4 mg (38%).

FAB-MS m/z 259 (M+H)$^+$; $^1$H-NMR (500 MHz, CDCl$_3$) δ 7.95 (d, 1H, J=1.8 Hz), 7.70 (dd, 1H, J=6.0, 1.8 Hz), 7.38 (d, 2H, J=2.4 Hz), 3.54 (septet, 1H, J=7.0 Hz), 1.70 (s, 4H), 1.31 (s, 6H), 1.29 (s, 6H), 1.21 (d, 6H, J=7.0 Hz).

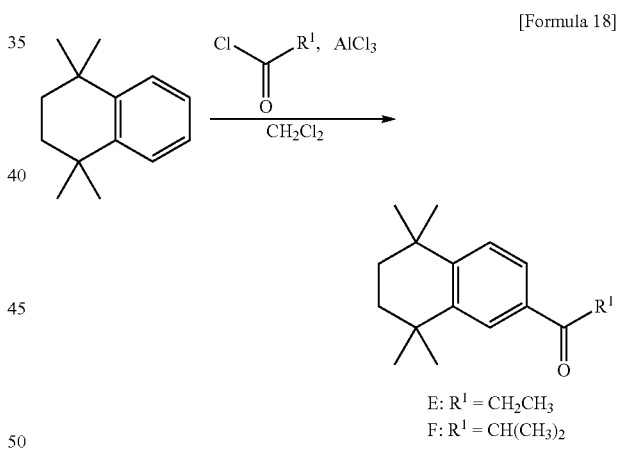

[Formula 18]

Example 7

Synthesis of 5,6,7,8-tetrahydro-3-hydroxy-5,5,8,8-tetramethyl-2-naphthyl ethanethione (G)

To 5,6,7,8-tetrahydro-3-hydroxy-5,5,8,8-tetramethyl-2-naphthyl methyl ketone (13.3 mg, 53.9 μmol) were added anhydrous toluene (1 mL) and Lawesson's reagent (32.0 mg, 80.9 mmol) followed by stirring at 120° C. for 24 hours. The reaction solution was poured into cold water and extracted by dichloromethane, and the combined organic layers were concentrated under reduced pressure. The crude product was purified by silica gel column chromatography using hexane/ethyl acetate (12/1) as an elution solvent. The yield was 4.2 mg (30%).

FAB-MS m/z 263 (M+H)$^+$; $^1$H-NMR (500 MHz, CDCl$_3$) δ 12.99 (s, 1H), 7.82 (s, 1H), 6.99 (s, 1H), 3.12 (s, 3H), 1.69 (s, 4H), 1.30 (s, 6H), 1.29 (s, 6H).

Comparative Example 1

Synthesis of 5,6,7,8-tetrahydro-5,5,8,8-tetramethyl-2-naphthyl-N-methoxy-N-methylamide (J)

(1) Synthesis of 5,6,7,8-tetrahydro-5,5,8,8-tetramethyl-2-methylnaphthalene (b)

The synthesis process is as set forth in the chemical reaction formula below. Into anhydrous toluene (10 mL) were added aluminum chloride (200 mg, 1.5 mmol), 2,5-dichloro-2,5-dimethylhexane (4.70 g, 25.7 mmol) followed by stirring at room temperature for 24 hours. The reaction solution was poured into cold water and extracted by ethyl acetate. The organic layer was washed by water, a saturated sodium hydrogen carbonate aq. solution, and a saturated saline solution, dried over magnesium sulfate, and concentrated under reduced pressure. The yield was 4.90 g (94%).

$^1$H-NMR (500 MHz, CDCl$_3$) δ 7.20 (d, 1H, J=8.0 Hz), 7.10 (d, 1H, J=1.2 Hz), 6.95 (dd, 1H, J=6.5, 1.2 Hz), 2.29 (s, 3H), 1.67 (s, 4H), 1.28 (s, 6H), 1.26 (s, 6H).

(2) Synthesis of 5,6,7,8-tetrahydro-5,5,8,8-tetramethyl-2-naphthalenecarboxylic acid (c)

The synthesis process is as set forth in the chemical reaction formula below. The KMnO$_4$ in the reaction path stands for potassium permanganate. To 5,6,7,8-tetrahydro-5,5,8,8-tetramethyl-2-methylnaphthalene (3.52 g, 17.4 mmol) were added pyridine (12 mL), potassium permanganate (6.70 g, 42.4 mmol), and sodium hydroxide (1.00 g, 25.0 mmol) followed by stirring at 95° C. for 5 hours. The reaction solution was filtrated by celite and the filtrate was made acidic by adding hydrochloric acid. After extraction by ethyl acetate, the liquid was dried over magnesium sulfate, and concentrated under reduced pressure. The crude product was purified by silica gel chromatography using hexane/ethyl acetate (4/1) as an elution solvent. The yield was 141.6 mg (3%).

FAB-MS m/z 233 (M+H)$^+$; $^1$H-NMR (500 MHz, CDCl$_3$) δ 8.05 (d, 1H, J=1.8 Hz), 7.82 (dd, 1H, J=6.0, 1.8 Hz), 7.40 (d, 1H, J=8.0 Hz), 1.71 (s, 4H), 1.32 (s, 6H), 1.30 (s, 6H).

(3) Synthesis of 5,6,7,8-tetrahydro-5,5,8,8-tetramethyl-2-naphthyl-N-methoxy-N-methylamide (J)

The synthesis process is as set forth in the chemical reaction formula below. The DMF in the reaction path stands for N,N-dimethylformamide, the (COCl)$_2$ for oxalyl chloride, the HN(OMe)Me for N-methoxy-N-methylamine hydrochloride, and the Et$_3$N for triethylamine. To 5,6,7,8-tetrahydro-5,5,8,8-tetramethyl-2-naphthalenecarboxylic acid (c) (232 mg, 1.00 mol) were added anhydrous dichloromethane (10 mL), oxalyl chloride (294 mg, 2.40 mmol), N,N-dimethylformamide (1 drop) followed by stirring at room temperature for 5 hours. The reaction solution was concentrated under reduced pressure. To the crude product were added anhydrous dichloromethane (10 mL), N-methoxy-N-methylamine hydrochloride (116 mg, 1.20 mmol), and triethylamine (4.00 mL, 28.7 mmol) followed by stirring at room temperature for 17 hours. The reaction solution was concentrated under reduced pressure and diluted by ethyl acetate. The solution was washed by dil. hydrochloric acid, water, a saturated sodium hydrogen carbonate aq. solution and a saturated saline solution, and the crude product was purified by silica gel chromatography using hexane/ethyl acetate (10/1) as an elution solvent. The yield was 139 mg (50%).

FAB-MS m/z 276 (M+H)$^+$; $^1$H-NMR (500 MHz, CDCl$_3$) δ 7.34 (d, 1H, J=1.8 Hz), 7.30 (d, 1H, J=8.0 Hz), 7.16 (dd, 1H, J=6.1, 1.8 Hz), 3.10 (br s, 1H), 3.00 (br s, 1H), 1.68 (s, 4H), 1.29 (s, 6H), 1.28 (s, 6H).

Example 8

Synthesis of 5,6,7,8-tetrahydro-5,5,8,8-tetramethyl-2-naphthyl amide (K)

The synthesis process is as set forth in the chemical reaction formula below. To 5,6,7,8-tetrahydro-5,5,8,8-tetramethyl-2-naphthalenecarboxylic acid (c) (465 mg, 2.00 mmol) were added DMF (3 drops), anhydrous dichloromethane (5 mL), and oxalyl chloride (0.25 mL, 2.95 mmol) followed by stirring at 0° C. for 1 hour. After adding conc. ammonia water (30 mL), the liquid was stirred at room temperature for 15 hours. The reaction solution added with water was extracted by dichloromethane. The organic layer was washed by water and a saturated saline solution, dried over magnesium sulfate, and concentrated under reduced pressure. The crude product was purified by recrystallization in ethyl acetate. The yield was 453 mg (98%).

FAB-MS m/z 232 (M+H)$^+$; $^1$H-NMR (500 MHz, CDCl$_3$) δ 7.81 (d, 1H, J=2.0 Hz), 7.49 (dd, 1H, J=8.0, 2.0 Hz), 1.70 (s, 4H), 1.31 (s, 6H), 1.29 (s, 6H).

Example 9

Synthesis of 5,6,7,8-tetrahydro-5,5,8,8-tetramethyl-2-naphthyl phenyl ketone (H)

The synthesis process is as set forth in the chemical reaction formula below. The PhBr in the reaction path stands for benzene bromide. To benzene bromide (1.17 g, 7.50 mmol) were added anhydrous tetrahydrofuran (10 mL), magnesium (911 mg, 37.5 mol) and iodine, followed by stirring at 80° C. After cooling down to room temperature, the mixture was added to 5,6,7,8-tetrahydro-5,5,8,8-tetramethyl-2-naphthyl-N-methoxy-N-methylamide (J) (55.0 mg, 0.200 mmol) dissolved in anhydrous diethyl ether (2 mL), which was then stirred at room temperature for 22 hours. The reaction solution was poured into a saturated ammonium chloride aq. solution and extracted by ethyl acetate. The organic layer was washed by water, a saturated sodium hydrogen carbonate aq. solution and a saturated saline solution, dried over magnesium sulfate, and concentrated under reduced pressure. The crude product was purified by silica gel chromatography using hexane/ethyl acetate (2/1) as an elution solvent. The yield was 14.9 mg (25%).

FAB-MS m/z 293 (M+H)$^+$; $^1$H-NMR (500 MHz, CDCl$_3$) δ 7.80 (d, 1H, J=7.3 Hz), 7.79 (s, 1H), 7.57 (t, 1H, J=7.5 Hz), 7.55 (dd, 1H, J=6.1, 1.8 Hz), 7.47 (t, 1H, J=8.0 Hz), 7.39 (d, 1H, J=8.0 Hz), 1.72 (s, 4H), 1.31 (s, 6H), 1.29 (s, 6H).

Example 10

Synthesis of 5,6,7,8-tetrahydro-5,5,8,8-tetramethyl-2-naphthaldehyde (I)

The synthesis process is as set forth in the chemical reaction formula below. The CAN in the reaction path stands for cerium ammonium nitrate. To 5,6,7,8-tetrahydro-5,5,8,8-tetramethyl-2-methylnaphthalene (b) (202 mg, 1.00 mol) were added acetic acid (8.2 mL) and cerium ammonium nitrate (2.40 g, 4.37 mol) followed by stirring at 100° C. for 1 hour. The reaction solution was poured into ice water and extracted by ethyl acetate. The organic layer was washed by water, a saturated sodium hydrogen carbonate aq. solution and a saturated saline solution, dried over magnesium sulfate, and concentrated under reduced pressure. The crude product was purified by silica gel chromatography using hexane/ethyl acetate (15/1) as an elution solvent. The yield was 106 mg (49%).

FAB-MS m/z 217 (M+H)+; 1H-NMR (500 MHz, CDCl3) δ 9.95 (s, 1H), 7.83 (d, 1H, J=2.0 Hz), 7.62 (dd, 1H, J=7.0, 2.0 Hz), 7.46 (d, 1H, J=8.0 Hz), 1.72 (s, 4H), 1.32 (s, 6H), 1.31 (s, 6H).

[Formula 19]

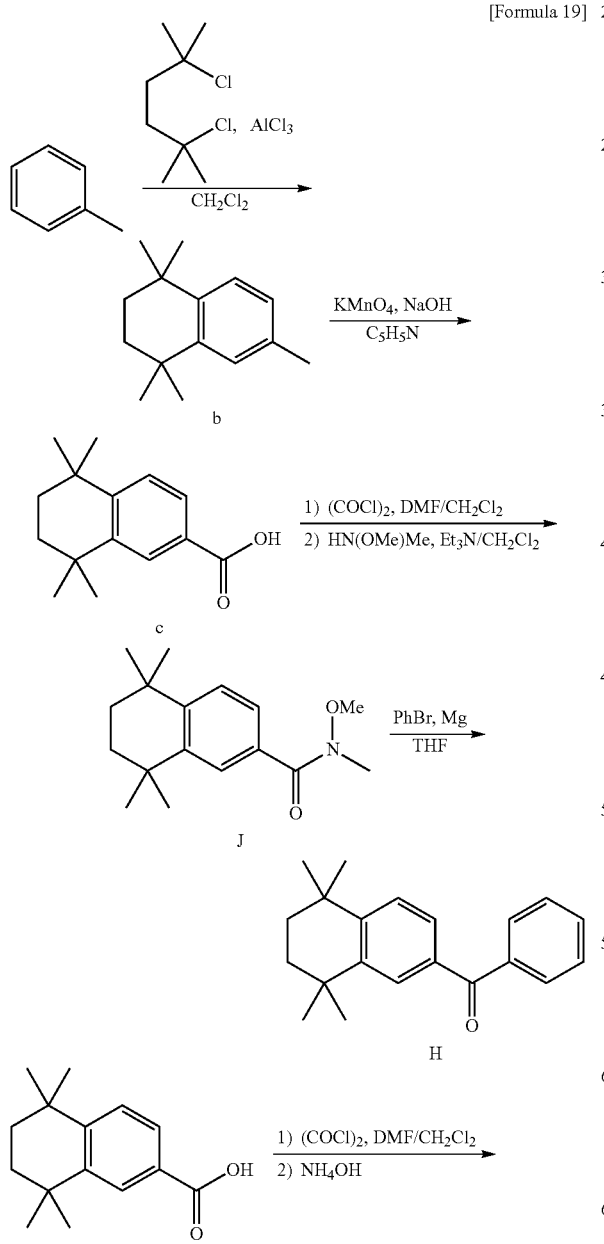

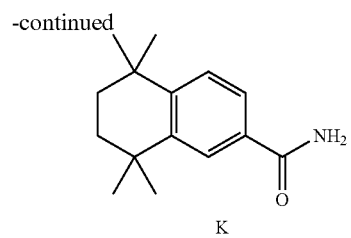

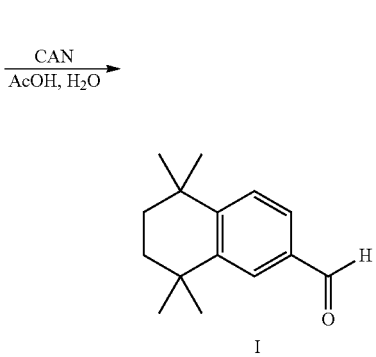

Example 11

Synthesis of 5,6,7,8-tetrahydro-5,8-disila-5,5,8,8-tetramethyl-2-naphthyl methyl ketone (L)

The synthesis process is as set forth below according to the description of Buttner M. W, Penka M, Doszczak L, Kraft P, Tacke R, "Silicon Analogues of the Musk Odorant Versalide", Organometallics 26: 1295-1298 (2007).

(1) Synthesis of 5,6,7,8-tetrahydro-5,8-disila-5,5,8,8-tetramethyl-2-naphthyl ethan-1-ol (d)

To 1,2-bis(ethynyldimethylsilyl)ethane (486 mg, 2.50 mmol) and 3-(trimethylsiloxy)-1-butyne (498 mg, 3.50 mol) were added anhydrous xylene (5 mL) and cyclopentadienylcobalt dicarbonyl (135 mg, 0.750 mmol) followed by heating at 170° C. for 9 hours. The reaction solution was concentrated under reduced pressure. The residue was partially purified by silica gel chromatography using hexane/ethyl acetate (20/1) as an elution solvent. To the crude product were added methanol (5 mL) and acetic acid (1 mL), and the mixture was heated at 95° C. for 30 hours. The reaction liquid was poured into a saturated sodium hydrogen carbonate aq. solution, followed by extraction by ethyl acetate. The organic layer was washed by water and a saturated saline solution, dried over magnesium sulfate, and concentrated under reduced pressure. The crude product was purified by silica gel chromatography using hexane/ethyl acetate (4/1) as an elution solvent. The yield was 153 mg (23%).

1H-NMR (500 MHz, CDCl3) δ 7.50 (m, 2H), 7.36 (dd, 1H, J=6.0, 2.0 Hz), 4.87 (m, 1H), 1.51 (d, 3H), 1.00 (s, 4H), 0.23 (d, 6H, J=2.0 Hz), 0.22 (s, 6H).

(2) Synthesis of 5,6,7,8-tetrahydro-5,8-disila-5,5,8,8-tetramethyl-2-naphthyl methyl ketone (L)

To 5,6,7,8-tetrahydro-5,8-disila-5,5,8,8-tetramethyl-2-naphthyl ethan-1-ol (d) (153 mg, 0.577 mmol) were added dichloromethane (2 mL) and pyridinium dichromate (376 mg, 1.00 mmol) followed by stirring at room temperature for 2 hours. The reaction solution was filtrated by celite, washed by dichloromethane, and then concentrated under reduced pressure. The crude product was purified by silica gel chromatography using hexane/ethyl acetate (8/1) as an elution solvent. The yield was 67.9 mg (45%).

FAB-MS m/z 263 (M+H)$^+$; $^1$H-NMR (500 MHz, CDCl$_3$) δ 8.05 (d, 1H, J=6.0, 2.0 Hz), 7.86 (dd, 1H, J=6.0, 2.0 Hz), 7.60 (d, 1H, J=7.0 Hz), 2.60 (s, 3H), 1.03 (s, 4H), 0.26 (s, 6H), 0.24 (s, 6H).

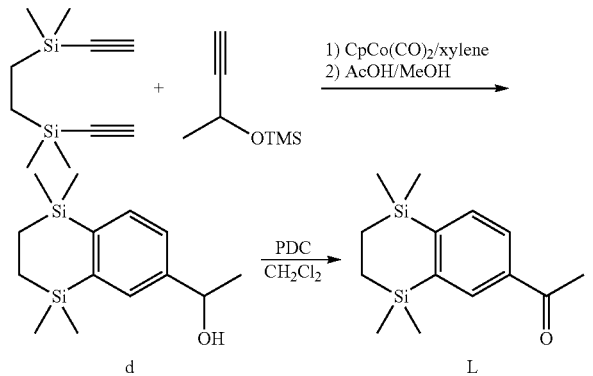

[Formula 20]

Example 12

Synthesis of 5,6,7,8-tetrahydro-3-hydroxy-5,5,8,8-tetramethyl-2-naphthyl 13-(N,N-dimethylamino) vinyl ketone (M)

The synthesis process is as set forth in the chemical reaction formula below. To 5,6,7,8-tetrahydro-3-hydroxy-5,5,8,8-tetramethyl-2-naphthyl methyl ketone (TMNAA) (129 mg, 0.50 mmol) were added N,N-dimethylformamide (0.5 mL) and N,N-dimethylformamide dimethyl acetal (135 µL, 1.01 mmol), followed by stirring at 100° C. for 3.5 hours. The reaction solution was poured into ice water and extracted by diethyl ether. The organic layer was washed by water and a saturated saline solution, dried over magnesium sulfate, and concentrated under reduced pressure. The yield was 151 mg (100%).

FAB-MS m/z 302 (M+H)$^+$; 1H-NMR (500 MHz, CDCl$_3$) δ 13.42 (s, 1H), 7.87 (d, 1H, J=12.0 Hz), 7.59 (s, 1H), 6.86 (s, 1H), 5.76 (d, 1H, J=12.0 Hz), 3.18 (s, 3H), 2.99 (s, 3H), 1.67 (s, 4H), 1.29 (s, 6H), 1.27 (s, 6H).

Example 13

Synthesis of 6,7,8,9-tetrahydro-6,6,9,9-tetramethyl-4H-naphtho[2,3-b]pyran-4-one (N)

The synthesis process is as set forth in the chemical reaction formula below. To 5,6,7,8-tetrahydro-3-hydroxy-5,5,8,8-tetramethyl-2-naphthyl-β-(N,N-dimethylamino)vinylketone (the above named compound M) (149 mg, 0.50 mmol) was added 3N sulfuric acid (0.5 mL) followed by stirring at 105° C. for 3.5 hours. The reaction solution was poured into a saturated sodium hydrogen carbonate aq. solution and extracted by ethyl acetate. The organic layer was dried over magnesium sulfate, and concentrated under reduced pressure. The yield was 125 mg (98%).

FAB-MS m/z 257 (M+H)$^+$; 1H-NMR (500 MHz, CDCl$_3$) δ 8.14 (s, 1H), 7.79 (d, 1H, J=6.0 Hz), 7.36 (s, 1H), 6.26 (d, 1H, J=6.0 Hz), 1.73 (s, 4H), 1.34 (s, 6H), 1.33 (s, 6H).

Example 14

Synthesis of 2,3,6,7,8,9-hexahydro-6,6,9,9-tetramethyl-4H-naphtho[2,3-b]pyran-4-one (O)

The synthesis process is as set forth in the chemical reaction formula below. To 6,7,8,9-tetrahydro-6,6,9,9-tetramethyl-4H-naphtho[2,3-b]pyran-4-one (the above named compound N) (124 mg, 0.48 mmol) were added methanol (4.0 mL), ethyl acetate (4.0 mL) and 10% palladium on carbon (40 mg), followed by stirring under a hydrogen atmosphere at room temperature for 10 hours. The reaction solution was filtrated by celite, and the filtrate was concentrated under reduced pressure. The crude product was purified by silica gel chromatography using hexane/ethyl acetate (4/1 to 2/1) as an elution solvent. The yield was 80.0 mg (64%).

FAB-MS m/z 259 (M+H)$^+$; 1H-NMR (500 MHz, CDCl$_3$) δ 7.85 (s, 1H), 6.89 (s, 1H), 4.50 (t, 2H, J=6.0 Hz), 2.77 (t, 2H, J=6.0 Hz), 1.67 (s, 4H), 1.27 (s, 6H), 1.26 (s, 6H).

[Formula 21]

(Demonstration of Anti ATL Effect of Agent)

In the presence of various concentrations of agents, SIT (cell strain originated from an ATL patient) and as a control MOLT-4 (acute lymphoblastic leukemia cell strain) were cultivated for 4 days, and the growth inhibitory effects of the compounds on the respective cells were evaluated by the MTT method. The results are shown in Table 2.

TABLE 2

Anti ATL effect of agent

| Agent | IC$_{50}$ (μM) S1T cell | IC$_{50}$ (μM) MOLT-4 cell | SI |
|---|---|---|---|
| A | 4.7 ± 1.3 | 32.3 ± 5.4 | 6.9 |
| B | 6.0 ± 0.7 | 31.9 ± 0.2 | 5.3 |
| C | 41.5 ± 0.8 | 43.2 ± 2.4 | 1.0 |
| D | 15.2 ± 2.3 | 28.3 ± 0.7 | 1.9 |
| E | 3.3 ± 1.0 | 21.5 ± 2.2 | 6.5 |
| F | 3.8 ± 2.1 | 34.6 ± 1.5 | 9.1 |
| G | 6.9 ± 2.3 | 36.4 ± 2.1 | 5.3 |
| H | 7.0 ± 0.9 | 11.8 ± 2.2 | 1.7 |
| J | 12.6 ± 2.1 | 9.9 ± 0.0 | <1.0 |
| K | 37.0 ± 2.1 | 39.4 ± 10.4 | 1.1 |
| M | 2.1 ± 0.1 | 9.3 ± 0.9 | 4.4 |
| N | 1.9 ± 0.2 | 14.5 ± 1.9 | 7.6 |
| O | 6.7 ± 0.9 | 13.6 ± 2.6 | 2.0 |

S1T (cell strain originated from an ATL patient) and MOLT-4 (acute lymphoblastic leukemia cell strain) as a control were cultivated for 4 days in the presence of various concentrations of agents, and then the viable cell counts were quantified by the MTT method.
IC50: Concentration of an agent to inhibit cell growth by 50%.
SI: Selectivity to ATL cell (IC50 for MOLT-4/IC50 for S1T).
The values are mean values of at least 2 experiments.

As obvious from the results in Table 2, the compounds according to the present invention have higher selectivity to the ATL cell than another derivative having an analogous structure (the agent J).

The contents of the publications, patents and patent applications cited heron are incorporated herein by reference in their entirety.

The invention claimed is:

1. A method for treating adult T-cell leukemia comprising administering to a subject in need thereof a therapeutically effective amount of a compound represented by the formula I:

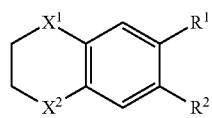

I wherein
R$^1$ is H, OH, an alkoxy group, a linear or branched, saturated or unsaturated aliphatic acyl group containing 1 to 10 carbon atoms, a benzoyl group, a naphthoyl group, a linear or branched, saturated or unsaturated aliphatic thioacyl group containing 1 to 10 carbon atoms, a thiobenzoyl group, or a thionaphthoyl group, and
R$^2$ is a linear or branched, saturated or unsaturated aliphatic acyl group containing 1 to 10 carbon atoms, a benzoyl group, a naphthoyl group, a linear or branched, saturated or unsaturated aliphatic thioacyl group containing 1 to 10 carbon atoms, a thiobenzoyl group, a thionaphthoyl group, CONR$^7$R$^8$, or CSNR$^7$R$^8$, wherein R$^7$ and R$^8$ are each independently selected from H, an alkyl group containing 1 to 3 carbon atoms, or a phenyl group, or
R$^1$ and R$^2$ together form a ring as represented by —OCH$_2$CH$_2$CO— or —OCH=CHCO—,
X$^1$ and X$^2$ are each independently selected from —CR$^3$R$^4$— and —SiR$^3$R$^4$—, and
R$^3$ and R$^4$ are each independently selected from an alkyl group containing 1 to 6 carbon atoms; wherein the compound represented by the formula I is a compound represented by the following formula:

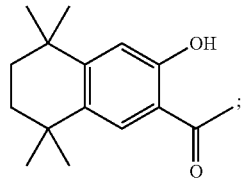 III

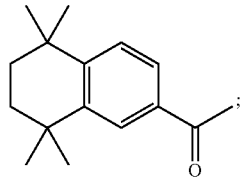 IV

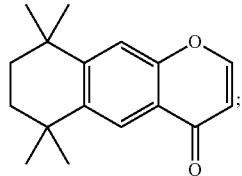 VI

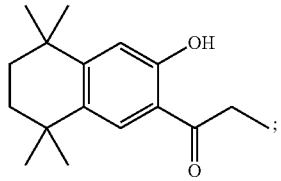 A

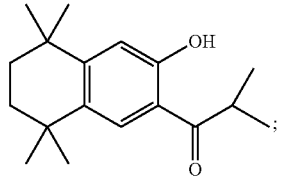 B

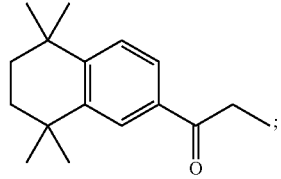 E

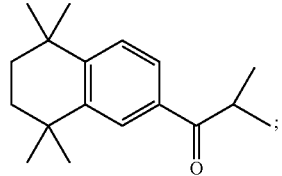 F

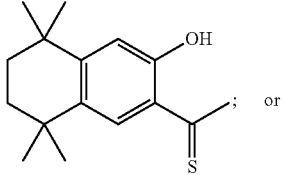 G or

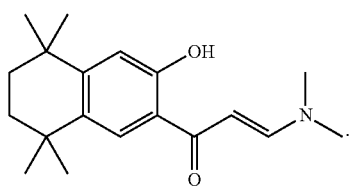
M

2. The method of claim 1, wherein the compound represented by the formula I is a compound represented by formula III:

III

3. The method of claim 1, wherein the compound represented by the formula I is a compound represented by formula IV:

IV

4. The method of claim 1, wherein the compound represented by the formula I is a compound represented by formula VI:

VI

5. The method of claim 1, wherein the compound represented by the formula I is a compound represented by formula A:

A

6. The method of claim 1, wherein the compound represented by the formula I is a compound represented by formula B:

B

7. The method of claim 1, wherein the compound represented by the formula I is a compound represented by formula E:

E

8. The method of claim 1, wherein the compound represented by the formula I is a compound represented by formula F:

F

9. The method of claim 1, wherein the compound represented by the formula I is a compound represented by formula G:

G

10. The method of claim 1, wherein the compound represented by the formula I is a compound represented by formula M:
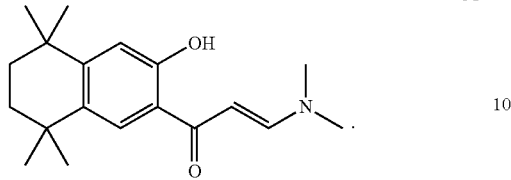
M
* * * * *